US009241761B2

(12) United States Patent
Rankin et al.

(10) Patent No.: US 9,241,761 B2
(45) Date of Patent: *Jan. 26, 2016

(54) ABLATION PROBE WITH ULTRASONIC IMAGING CAPABILITY

(71) Applicants: Boston Scientific Scimed, Inc., Maple Grove, MN (US); Koninklijke Philips N.V., Eindhoven (NL)

(72) Inventors: Darrell L. Rankin, Milpitas, CA (US); Josef V. Koblish, Sunnyvale, CA (US); Szabolcs Deladi, Veldhoven (NL)

(73) Assignees: Koninklijke Philips N.V., Eindhoven (NL); Boston Scientific Scimed Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,685

(22) Filed: Dec. 28, 2012

(65) Prior Publication Data

US 2013/0172742 A1     Jul. 4, 2013

Related U.S. Application Data

(60) Provisional application No. 61/580,705, filed on Dec. 28, 2011.

(51) Int. Cl.
*A61B 8/00* (2006.01)
*A61B 18/14* (2006.01)
(Continued)

(52) U.S. Cl.
CPC .............. *A61B 18/1492* (2013.01); *A61B 8/12* (2013.01); *A61B 8/445* (2013.01); *A61B 8/4477* (2013.01); *A61B 8/5207* (2013.01); *A61B 8/54* (2013.01);
(Continued)

(58) Field of Classification Search
None
See application file for complete search history.

(56) References Cited

U.S. PATENT DOCUMENTS 3,773,401 A    11/1973  Douklias et al.
4,763,660 A     8/1988  Kroll et al.
(Continued)

FOREIGN PATENT DOCUMENTS

CN    104619259 A    5/2015
CN    104661609 A    5/2015
(Continued)

OTHER PUBLICATIONS

International Search Report and Written Opinion issued in PCT/US2012/055309, mailed Nov. 19, 2012, 13 pages.
(Continued)

*Primary Examiner* — Amanda Lauritzen Moher
*Assistant Examiner* — Shahdeep Mohammed
(74) *Attorney, Agent, or Firm* — Faegre Baker Daniels LLP (57) ABSTRACT

Devices and systems for ultrasonically imaging anatomical structures and performing ablation therapy within the body are disclosed. A combined ablation and ultrasound imaging probe includes an ablation electrode tip including an ablation electrode configured for delivering ablation energy, and a number of ultrasonic imaging sensors configured for imaging the tissue surrounding the probe. The ultrasonic imaging sensors are supported within the interior of the tip via a tip insert, and deliver ultrasonic waves through acoustic openings formed through the tip. The tip insert separates an interior lumen within the tip into a proximal fluid chamber and a distal fluid chamber. During an ablation procedure, the ultrasonic imaging sensors can be tasked to generate a number of ultrasonic images that can be displayed on a user interface.

19 Claims, 6 Drawing Sheets

(51) Int. Cl.
*A61B 8/12* (2006.01)
*A61M 5/00* (2006.01)
*A61B 8/08* (2006.01)
*A61B 18/12* (2006.01)
A61B 19/00 (2006.01)
A61B 17/00 (2006.01)
A61B 18/00 (2006.01)

(52) U.S. Cl.
CPC .............. *A61B 18/1206* (2013.01); *A61M 5/00* (2013.01); *A61B 2017/003* (2013.01); *A61B 2017/00106* (2013.01); *A61B 2018/00023* (2013.01); *A61B 2018/00577* (2013.01); *A61B 2018/00821* (2013.01); *A61B 2018/00982* (2013.01); *A61B 2019/528* (2013.01); *A61B 2019/5466* (2013.01); *A61B 2217/007* (2013.01)

(56) References Cited

U.S. PATENT DOCUMENTS

| | | |
|---|---|---|
| 5,029,588 A | 7/1991 | Yock et al. |
| 5,178,150 A | 1/1993 | Silverstein et al. |
| 5,240,003 A | 8/1993 | Lancee et al. |
| 5,254,088 A | 10/1993 | Lundquist et al. |
| 5,331,966 A | 7/1994 | Bennett et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,462,521 A | 10/1995 | Brucker et al. |
| 5,485,849 A | 1/1996 | Panescu et al. |
| 5,494,042 A | 2/1996 | Panescu et al. |
| 5,500,012 A | 3/1996 | Brucker et al. |
| 5,571,088 A | 11/1996 | Lennox et al. |
| 5,579,764 A | 12/1996 | Goldreyer |
| 5,582,609 A | 12/1996 | Swanson et al. |
| 5,647,870 A | 7/1997 | Kordis et al. |
| 5,762,067 A | 6/1998 | Dunham et al. |
| 5,788,636 A | 8/1998 | Curley |
| 5,800,482 A | 9/1998 | Pomeranz et al. |
| 5,830,213 A | 11/1998 | Panescu et al. |
| 5,833,621 A | 11/1998 | Panescu et al. |
| 5,868,735 A | 2/1999 | Lafontaine |
| 5,871,483 A | 2/1999 | Jackson et al. |
| 6,004,269 A | 12/1999 | Crowley et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,083,170 A | 7/2000 | Ben-Haim |
| 6,101,409 A | 8/2000 | Swanson et al. |
| 6,116,027 A | 9/2000 | Smith et al. |
| 6,165,123 A * | 12/2000 | Thompson .................. 600/152 |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,290,697 B1 | 9/2001 | Tu et al. |
| 6,352,534 B1 | 3/2002 | Paddock et al. |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,516,667 B1 | 2/2003 | Broad et al. |
| 6,517,533 B1 | 2/2003 | Swaminathan |
| 6,537,271 B1 | 3/2003 | Murray et al. |
| 6,544,175 B1 | 4/2003 | Newman |
| 6,547,788 B1 | 4/2003 | Maguire et al. |
| 6,572,549 B1 | 6/2003 | Jong et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,656,174 B1 | 12/2003 | Hegde et al. |
| 6,658,279 B2 | 12/2003 | Swanson et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,811,550 B2 | 11/2004 | Holland et al. |
| 6,824,517 B2 | 11/2004 | Salgo et al. |
| 6,837,884 B2 | 1/2005 | Woloszko |
| 6,917,834 B2 | 7/2005 | Koblish et al. |
| 6,922,579 B2 | 7/2005 | Taimisto et al. |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,105,122 B2 | 9/2006 | Karason |
| 7,112,198 B2 | 9/2006 | Satake |
| 7,115,122 B1 | 10/2006 | Swanson et al. |
| 7,131,947 B2 | 11/2006 | Demers |
| 7,166,075 B2 | 1/2007 | Varghese et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |

(56) References Cited

U.S. PATENT DOCUMENTS

| | | |
|---|---|---|
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,892,228 B2 | 2/2011 | Landis et al. |
| 8,016,822 B2 | 9/2011 | Swanson |
| 8,740,900 B2 | 6/2014 | Kim et al. |
| 2002/0087208 A1 | 7/2002 | Koblish et al. |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0270794 A1 | 11/2007 | Anderson et al. |
| 2008/0009733 A1 | 1/2008 | Saksena |
| 2008/0025145 A1 | 1/2008 | Peszynski et al. |
| 2008/0058836 A1 | 3/2008 | Moll et al. |
| 2008/0091109 A1 | 4/2008 | Abraham |
| 2008/0140065 A1 | 6/2008 | Rioux et al. |
| 2008/0161795 A1 | 7/2008 | Wang et al. |
| 2008/0195089 A1 | 8/2008 | Thiagalingam et al. |
| 2008/0228111 A1 | 9/2008 | Nita |
| 2008/0243214 A1* | 10/2008 | Koblish ............... 607/115 |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2009/0030312 A1 | 1/2009 | Hadjicostis |
| 2009/0048591 A1 | 2/2009 | Ibrahim et al. |
| 2009/0062790 A1 | 3/2009 | Malchano et al. |
| 2009/0076390 A1 | 3/2009 | Lee et al. |
| 2009/0093810 A1* | 4/2009 | Subramaniam et al. ........ 606/41 |
| 2009/0093811 A1 | 4/2009 | Koblish et al. |
| 2009/0182316 A1 | 7/2009 | Bencini |
| 2009/0216125 A1* | 8/2009 | Lenker ..................... 600/445 |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2009/0292209 A1 | 11/2009 | Hadjicostis |
| 2009/0299360 A1 | 12/2009 | Ormsby |
| 2010/0010487 A1 | 1/2010 | Phan et al. |
| 2010/0057072 A1 | 3/2010 | Roman et al. |
| 2010/0106155 A1 | 4/2010 | Anderson et al. |
| 2010/0113938 A1 | 5/2010 | Park et al. |
| 2010/0168568 A1* | 7/2010 | Sliwa ..................... 600/439 |
| 2010/0168570 A1 | 7/2010 | Sliwa et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0071400 A1 | 3/2011 | Hastings et al. |
| 2011/0071401 A1 | 3/2011 | Hastings et al. |
| 2011/0125143 A1 | 5/2011 | Gross et al. |
| 2011/0130648 A1* | 6/2011 | Beeckler et al. ............... 600/424 |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2012/0095347 A1 | 4/2012 | Adam et al. |
| 2012/0136351 A1 | 5/2012 | Weekamp et al. |
| 2012/0172698 A1 | 7/2012 | Teo et al. |
| 2012/0172727 A1 | 7/2012 | Hastings et al. |
| 2012/0172871 A1 | 7/2012 | Hastings et al. |
| 2012/0310064 A1 | 12/2012 | McGee |
| 2012/0330304 A1 | 12/2012 | Vegesna et al. |
| 2013/0023897 A1 | 1/2013 | Wallace |
| 2013/0066312 A1 | 3/2013 | Subramaniam et al. |
| 2013/0066315 A1 | 3/2013 | Subramaniam et al. |
| 2013/0197363 A1 | 8/2013 | Rankin et al. |
| 2014/0066764 A1 | 3/2014 | Subramaniam et al. |
| 2014/0081262 A1 | 3/2014 | Koblish et al. |
| 2014/0276052 A1 | 9/2014 | Rankin et al. |
| 2015/0133920 A1 | 5/2015 | Rankin et al. |

FOREIGN PATENT DOCUMENTS

| | | |
|---|---|---|
| EP | 1343426 B1 | 9/2003 |
| EP | 1343427 B1 | 9/2003 |
| EP | 1547537 A1 | 6/2005 |
| EP | 1717601 A2 | 11/2006 |
| EP | 1935332 A2 | 6/2008 |
| JP | 2000000242 A | 1/2000 |
| JP | 2006239414 A | 9/2006 |
| JP | 2007163559 A | 6/2007 |
| JP | 2009142653 A | 12/2008 |
| JP | 2010522623 A | 7/2010 |
| JP | 2015509027 A | 3/2015 |
| WO | WO9927862 A1 | 6/1999 |
| WO | WO0029062 A2 | 5/2000 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2009032421 A2 | 3/2009 |
| WO | 2010082146 A1 | 7/2010 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |

(56) References Cited

FOREIGN PATENT DOCUMENTS

| WO | WO2012001595 A1 | 1/2012 |
|---|---|---|
| WO | WO2012049621 A1 | 4/2012 |
| WO | WO2012066430 A1 | 5/2012 |

OTHER PUBLICATIONS

International Search Report and Written Opinion issued in PCT/US2012/072061, mailed Mar. 21, 2013, 9 pages.
International Search Report and Written Opinion issued in PCT/US2013/020503, mailed Mar. 20, 2013, 10 pages.
Partial International Search Report issued in PCT/US2012/0551545, mailed Dec. 20, 2012, 7 pages.
International Search Report and Written Opinion issued in PCT/US2012/031819, mailed Sep. 27, 2012, 16 pages.
Goldberg, S. Nahum et al., "Variables Affecting Proper System Grounding for Radiofrequency Ablation in an Animal Model", JVIR, vol. 11, No. 8, Sep. 2000, pp. 1069-1075.
International Search Report and Written Opinion issued in PCT/US2008/058324, dated Aug. 18, 2008, 11 pages.
International Search Report and Written Opinion issued in PCT/US2013/058105, mailed Nov. 22, 2013, 16 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
International Search Report and Written Opinion issued in PCT/US2013/060612, mailed Feb. 28, 2014, 16 pages.
International Search Report and Written Opinion issued in PCT/US2014/027491, mailed Sep. 23, 2014, 17 pages.
Invitation to Pay Additional Fees and Partial International Search Report issued in PCT/US2014/027491, mailed Jul. 28, 2014, 5 pages.
International Preliminary Examination Report issued in PCT/US2013/060612, completed Mar. 24, 2015, 10 pages.
International Preliminary Report on Patentability issued in PCT/US2013/058105, completed Mar. 10, 2015.

\* cited by examiner

# ABLATION PROBE WITH ULTRASONIC IMAGING CAPABILITY

CROSS-REFERENCE TO RELATED APPLICATION

This application claims priority to Provisional Application No. 61/580,705, filed Dec. 28, 2011, which is herein incorporated by reference in its entirety.

TECHNICAL FIELD

The present disclosure relates generally to devices and systems for imaging tissue within the body during an ablation procedure. More specifically, the present disclosure relates to an ablation probe with ultrasonic imaging capabilities.

BACKGROUND

In ablation therapy, it is often necessary to determine various characteristics of body tissue at a target ablation site within the body. In interventional cardiac electrophysiology (EP) procedures, for example, it is often necessary for the physician to determine the condition of cardiac tissue at a target ablation site in or near the heart. During some EP procedures, the physician may deliver a mapping catheter through a main vein or artery into an interior region of the heart to be treated. Using the mapping catheter, the physician may then determine the source of a cardiac rhythm disturbance or abnormality by placing a number of mapping elements carried by the catheter into contact with the adjacent cardiac tissue and then operate the catheter to generate an electrophysiology map of the interior region of the heart. Once a map of the heart is generated, the physician may then advance an ablation catheter into the heart, and position an ablation electrode carried by the catheter tip near the targeted cardiac tissue to ablate the tissue and form a lesion, thereby treating the cardiac rhythm disturbance or abnormality. In some techniques, the ablation catheter itself may include a number of mapping electrodes, allowing the same device to be used for both mapping and ablation.

Various ultrasound-based imaging catheters and probes have been developed for directly visualizing body tissue in applications such as interventional cardiology, interventional radiology, and electrophysiology. For interventional cardiac electrophysiology procedures, for example, ultrasound imaging devices have been developed that permit the visualization of anatomical structures of the heart directly and in real-time. In some electrophysiology procedures, for example, ultrasound catheters may be used to image the intra-atrial septum, to guide transseptal crossing of the atrial septum, to locate and image the pulmonary veins, and to monitor the atrial chambers of the heart for signs of a perforation and pericardial effusion.

Many ultrasound-based imaging systems comprise an imaging probe that is separate from the mapping and ablation catheters used to perform therapy on the patient. As a result, a position tracking system is sometimes used to track the location of each device within the body. In some procedures, it may be difficult for the physician to quickly and accurately determine the condition of tissue to be ablated. Moreover, the images obtained using many ultrasound-based imaging systems are often difficult to read and understand without reference to images obtained from a separate imaging system such as a fluoroscopic imaging system.

SUMMARY

The present disclosure relates generally to devices and systems for imaging anatomical structures within the body during an ablation procedure.

In Example 1, an ablation probe for treating and imaging body tissue comprises: an ablation electrode tip including an ablation electrode configured for delivering ablation energy to body tissue; a plurality of acoustic openings disposed through the ablation electrode tip; a distal tip insert disposed within an interior lumen of the ablation electrode tip, the distal tip insert including a plurality of fluid channels; and a plurality of ultrasonic imaging sensors coupled to the distal tip insert, the ultrasonic imaging sensors configured to transmit ultrasonic waves through the acoustic openings.

In Example 2, the probe according to Example 1, wherein the ablation electrode tip comprises a tubular-shaped metal shell.

In Example 3, the probe according to any of Examples 1 or 2, wherein the distal tip insert includes a plurality of recesses each configured for receiving an ultrasonic imaging sensor.

In Example 4, the probe according to any of Examples 1-3, wherein the interior lumen of the ablation electrode tip includes a proximal fluid chamber and a distal fluid chamber, and wherein the proximal and distal fluid chambers are separated by the distal tip insert and are fluidly coupled to each other via the fluid channels.

In Example 5, the probe according to any of Examples 1-4, wherein distal tip insert comprises a substantially cylindrically-shaped insert body having a proximal section and a distal section.

In Example 6, the probe according to Example 5, wherein the fluid channels extend lengthwise along the proximal section of the distal insert body.

In Example 7, the probe of according to any of Examples 1-5, wherein the ultrasonic imaging sensors are disposed circumferentially about the distal tip insert.

In Example 8, the probe according to any of Examples 1-7, wherein the fluid channels are disposed circumferentially about the distal tip insert.

In Example 9, the probe according to any of Examples 1-8, wherein the fluid channels are circumferentially offset from the ultrasonic imaging sensors.

In Example 10, the probe according to any of Examples 1-9, further comprising an elongate probe body coupled to the ablation electrode tip.

In Example 11, the probe according to any of Examples 1-10, further comprising a proximal tip insert coupling a distal section of the elongate probe body to the ablation electrode tip.

In Example 12, the probe according to any of Examples 1-11, further comprising a plurality of irrigation ports disposed through the ablation electrode tip.

In Example 13, the probe according to Example 12, wherein the irrigation ports are located about the ablation electrode tip distally and/or proximally of the acoustic openings.

In Example 14, the probe according to any of Examples 1-13, wherein the ultrasonic imaging sensors comprise a plurality of laterally-facing ultrasonic imaging sensors configured for transmitting ultrasonic waves from a side of the ablation electrode tip.

In Example 15, the probe according to Example 14, wherein the laterally-facing ultrasonic imaging sensors are each coupled to a recess within the distal tip insert.

In Example 16, the probe according to any of Examples 1-15, wherein the ultrasonic imaging sensors comprise at least one distally-facing ultrasonic imaging sensor configured for transmitting ultrasonic waves in a forward direction away from a distal end of the ablation electrode tip.

In Example 17, the probe according to Example 16, wherein the distal-facing ultrasonic imaging sensor is coupled to an internal bore within the distal tip insert.

In Example 18, an ablation probe for treating and imaging body tissue comprises: an elongate probe body having a proximal section and a distal section; an ablation electrode tip coupled to the distal section of the elongate probe body, the ablation electrode tip including an ablation electrode configured for delivering ablation energy to body tissue; a plurality of acoustic openings disposed through the ablation electrode tip; a distal tip insert disposed within an interior lumen of the ablation electrode tip, the distal tip insert separating the interior lumen into a proximal fluid chamber and a distal fluid chamber; a plurality of laterally-facing ultrasonic imaging sensors each coupled to a corresponding recess within the distal tip insert, the laterally-facing ultrasonic imaging sensors each configured to transmit ultrasonic waves from a side of the ablation electrode tip; a plurality of fluid channels disposed about an outer extent of the distal tip insert and circumferentially offset from the ultrasonic imaging sensors; and a distally-facing ultrasonic imaging sensor coupled to the distal insert, the distally-facing ultrasonic imaging sensor configured for transmitting ultrasonic waves in a forward direction away from a distal end of the ablation electrode tip.

In Example 19, an ablation and ultrasound imaging system comprises: a probe configured for delivering ablation energy to body tissue, the probe comprising an ablation electrode tip, a plurality of acoustic openings disposed through the ablation electrode tip, a distal tip insert disposed within an interior lumen of the ablation electrode tip, the distal tip insert including a plurality of fluid channels, and a plurality of ultrasonic imaging sensors coupled to the distal tip insert, the ultrasonic imaging sensors configured to transmit ultrasonic waves through the acoustic openings; an ablation therapy module configured for generating and supplying an electrical signal to the ablation electrode tip; and an ultrasound imaging module configured for processing ultrasonic imaging signals received from the ultrasonic imaging sensors.

In Example 20, the system according to Example 19, wherein the ultrasonic imaging module comprises: a signal generator configured to generate control signals for controlling each ultrasonic imaging sensor; and an image processor configured for processing electrical signals received from each ultrasonic imaging sensor and generating a plurality of ultrasonic images.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
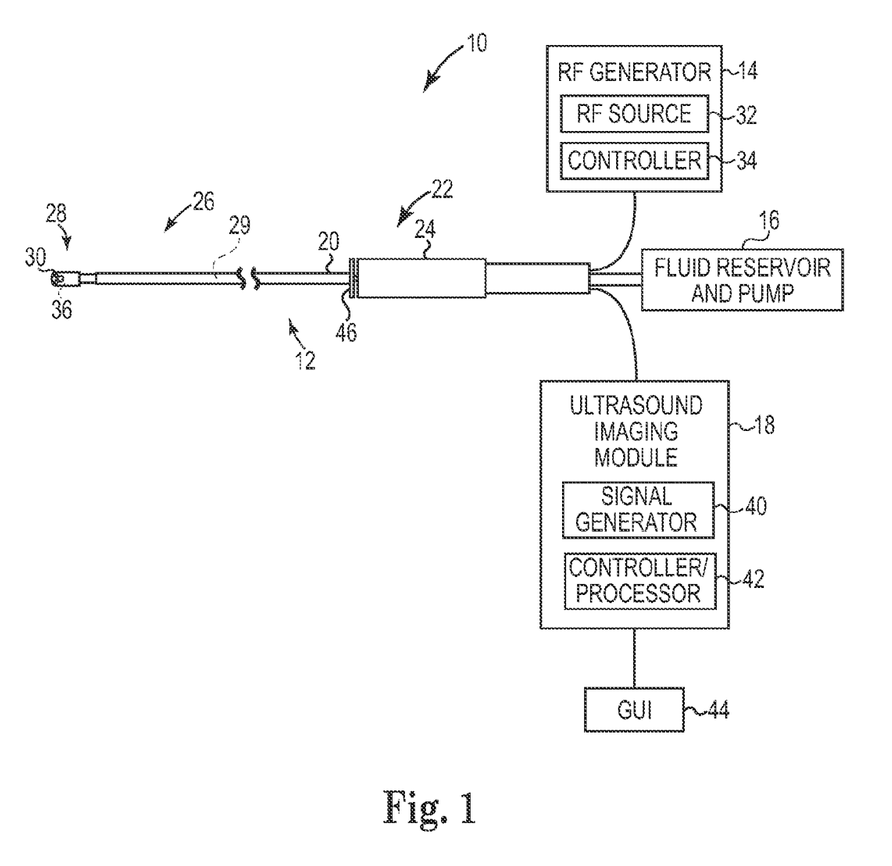
FIG. 1 is a schematic view of a combined ablation and imaging system in accordance with an illustrative embodiment.

FIG. 1 is a schematic view of a combined ablation and imaging system 10 in accordance with an illustrative embodiment. As shown in FIG. 1, the system 10 includes a combined ablation and ultrasonic imaging probe 12, an RF generator 14, a fluid reservoir and pump 16, and an ultrasonic imaging module 18. The probe 12 comprises an elongate probe body 20 having a proximal section 22 equipped with a handle assembly 24, and a deflectable distal section 26 including an ablation electrode tip 28. The probe body 20 includes an internal cooling fluid lumen 29 fluidly coupled to the fluid reservoir and pump 16, which supplies a cooling fluid, such as saline, through the probe body 20 to a number of irrigation ports 30 in the ablation electrode tip 28. The probe body 20 may further include additional lumens or other tubular elements for supporting electrical conductors, additional fluid lumens, a thermocouple, an insertable stylet, as well as other components. In some embodiments, the probe body 20 comprises flexible plastic tubing with a braided metal mesh to increase the rotational stiffness of the body 20.

The RF generator 14 is configured for generating RF energy for performing ablation procedures using the ablation electrode tip 28. The RF generator 14 includes an RF energy source 32 and a controller 34 for controlling the timing and level of the RF energy delivered by the tip 28. During an ablation procedure, the RF generator 14 is configured to deliver ablation energy to the tip 28 in a controlled manner to ablate any sites identified or targeted for ablation. Other types of ablation sources in addition to or in lieu of the RF generator 14 can also be used for ablating target sites. Examples of other types of ablation sources can include, but are not limited to, microwave generators, acoustic generators, cryoablation generators, and laser/optical generators.

The ultrasonic imaging module 18 is configured for generating high resolution ultrasonic images (e.g., A, M, or B-mode images) of anatomical structures within the body based on signals received from several ultrasonic imaging sensors 36 located within the probe tip 28. In the embodiment of FIG. 1, the ultrasonic imaging module 18 includes an ultrasonic signal generator 40 and an image processor 42. The ultrasonic signal generator 40 is configured to provide electrical signals for controlling each of the ultrasonic sensors 36. The imaging signals received back from the ultrasonic imaging sensors 36, in turn, are fed to the image processor 42, which processes the signals and generates images that can be displayed on a graphical user interface (GUI) 44. In certain embodiments, for example, the ultrasonic images displayed on the GUI 44 can be used to assist the physician with advancing the probe 12 through the body and to perform an ablation procedure. In cardiac ablation procedures, for example, the ultrasonic images generated from the ultrasound signals can be used to confirm tissue contact of the probe 12 within the heart or surrounding anatomy, to determine the orientation of the probe 12 within the body, to determine the tissue depth of the tissue at a target ablation site, and/or to visualize the progression of a lesion being formed in the tissue.

Various characteristics associated with the ultrasonic imaging sensors 36 as well as the circuitry within the ultrasonic imaging module 18 can be controlled to permit the sensors 36 to accurately detect tissue boundaries (e.g., blood or other bodily fluids), lesion formation and progression, as well as other characteristics of the tissue before, during, and/or after the ablation procedure. Example tissue characteristics that can be visualized using the probe 12 include, but are not limited to, the presence of fluid vaporization inside the tissue, the existence of a prior scar, the size and shape of a lesion being formed, as well as structures adjacent to heart tissue (e.g., lungs, esophagus). The depth at which the ultrasonic imaging sensors 36 can visualize anatomical structures within the body is dependent on the mechanical characteristics of the sensors 36, the electrical characteristics of the sensor circuitry including the drive frequency of the signal generator 40, the boundary conditions and degree of attenuation between the sensors 36 and the surrounding anatomy, as well as other factors.

In some embodiments, the probe 12 further includes a steering mechanism to permit the operator to deflect and steer the probe 12 within the body. In one embodiment, for example, a steering member such as a steering knob 46 rotatably coupled to the handle 24 can be used to deflect the ablation electrode tip 28 in one or multiple directions relative to a longitudinal axis of the probe body 20. Rotational movement of the steering knob 46 in a first direction relative to the handle 24 causes a steering wire within the probe body 20 to move proximally relative to the probe body 20, which, in turn, bends the distal section 26 of the probe body 20 into a particular shape such as an arced shape. Rotational movement of the steering knob 46 in the opposite direction, in turn, causes the distal section 26 of the probe body 20 to return to its original shape, as shown. To assist in the deflection, and in some embodiments, the probe body 20 includes one or more regions made of a lower durometer material than the other portions of the probe body 20.

Although the system 10 is described in the context of a medical system for use in intracardiac electrophysiology procedures for diagnosing and treating the heart, in other embodiments the system 10 may be used for treating, diagnosing, or otherwise visualizing other anatomical structures such as the prostate, brain, gall bladder, uterus, esophagus, and/or other regions in the body. Moreover, many of the elements in FIG. 1 are functional in nature, and are not meant to limit the structure that performs these functions in any manner. For example, several of the functional blocks can be embodied in a single device or one or more of the functional blocks can be embodied in multiple devices.

Figure 2:
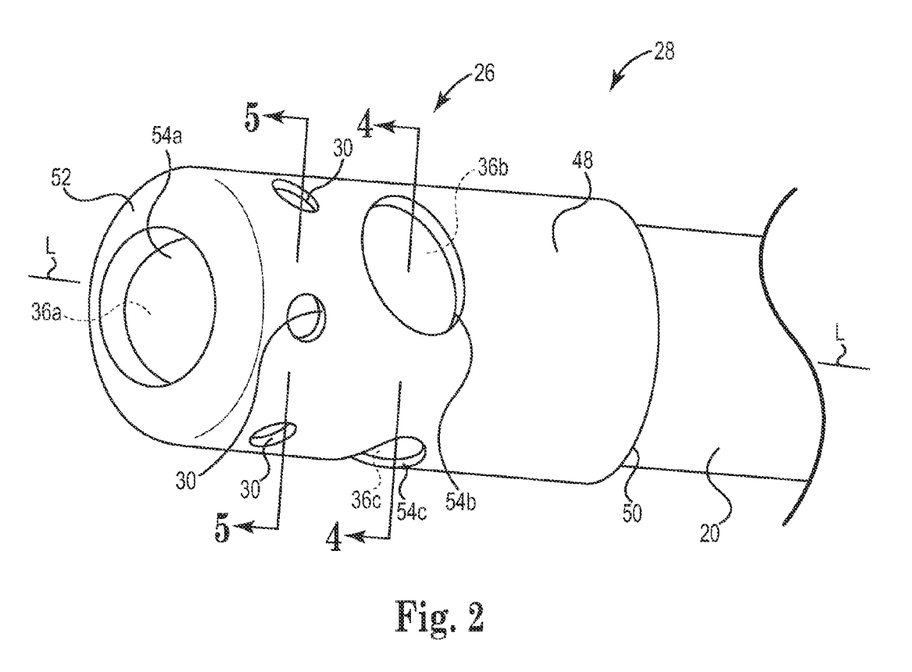
FIG. 2 is a perspective view showing the distal section of the combined ablation and imaging probe of FIG. 1 in greater detail.

FIG. 2 is a perspective view showing the distal section 26 of the probe 12 of FIG. 1 in greater detail. As can be further seen in FIG. 2, the ablation electrode tip 28 includes an RF ablation electrode 48 configured for delivering ablation energy to body tissue surrounding the tip 28. In the embodiment of FIG. 2, the RF ablation electrode 48 comprises a tubular-shaped metal shell that extends from a distal end 50 of the probe body 20 to a distal end 52 of the tip 28. A number of exposed openings 54a, 54b, 54c disposed through the ablation electrode tip 28 form acoustic openings that permit ultrasonic waves transmitted by the ultrasonic imaging sensors 36a, 36b, 36c, 36d to pass through the tip 28 and into the surrounding tissue. The reflected ultrasonic waves received back from the tissue pass through the acoustic openings 54a, 54b, 54c and are sensed by the ultrasonic imaging sensors 36a, 36b, 36c, 36d operating in a receive mode. In some embodiments, the acoustic openings 54a, 54b, 54c comprise exposed openings or apertures formed through the wall of the ablation electrode tip 28.

In addition to serving as an ablation electrode, the RF ablation electrode 48 also functions as a housing that contains the ultrasonic imaging sensors 36a, 36b, 36c, 36d, the electrical conductors coupling the RF ablation electrode 48 to the RF generator 14, the electrical conductors coupling the ultrasonic imaging sensors 36a, 36b, 36c, 36d to the ultrasonic imaging module 18, one or more steering wires of the steering mechanism, as well as other components. In certain embodiments, the RF ablation electrode 48 comprises an electrically conductive alloy such as platinum-iridium, which in addition to serving as an electrode for providing ablation therapy, is also used as a fluoroscopic marker to determine the location of the ablation electrode tip 28 within the body using fluoroscopy.

In the embodiment of FIG. 2, the probe 12 includes a distal-facing ultrasonic imaging sensor 36a located at or near the distal end 52 of the ablation electrode tip 28. In other embodiments, multiple distal-facing ultrasonic imaging sensors 36a are located at or near the distal end 52 of the ablation electrode tip 28. Each ultrasonic sensor 36a is configured to transmit ultrasonic waves primarily in a forward or distal direction away from the distal end 52 of the ablation electrode tip 28. A second set of ultrasonic imaging sensors 36b, 36c, 36d disposed within the tip 28 at a location proximal to the distal-facing ultrasonic imaging sensor 36a are configured to transmit ultrasonic waves primarily in a lateral or side-facing direction away from the side of the ablation electrode tip 28. The reflected waves received back from the ultrasonic imaging sensors 36a, 36b, 36c, 36d produces signals that can be used by the ultrasonic imaging module 18 to generate images of the surrounding body tissue.

In some embodiments, the ultrasonic imaging sensors 36a, 36b, 36c, 36d each comprise piezoelectric transducers formed of a piezoceramic material such as lead zirconate titanate (PZT) or a piezoelectric polymer such as polyvinylidene fluoride (PVDF). In some embodiments, the ablation electrode tip 28 includes three laterally-facing ultrasonic imaging sensors 36b, 36c, 36d each oriented circumferentially at 120° intervals apart from each other about the tip 28 for use in imaging tissue located adjacent to the sides of the tip 28. In other embodiments, a greater or lesser number of laterally-facing ultrasonic imaging sensors are employed for imaging tissue adjacent to the sides of the probe tip 28.

In the embodiment of FIG. 2, the ablation electrode tip 28 has an open irrigated configuration including a number of irrigation ports 30 used to deliver cooling fluid to cool the tip 28 and the surrounding tissue. In other embodiments, the ablation electrode tip 28 has a closed irrigation configuration in which the cooling fluid is recirculated through the tip 28 without being ejected into the surrounding tissue. In some embodiments, the ablation electrode tip 28 comprises six irrigation ports 30 each disposed circumferentially at 60° intervals apart from each other about the tip 28 and at a location proximal to the distal-facing ultrasonic sensor 36a and distal to the location of the laterally-facing ultrasonic sensors 36b, 36c, 36d. In other embodiments, a greater or lesser number of fluid irrigation ports 30 are employed. In some embodiments, the fluid irrigation ports 30 are circular in shape, and have a diameter in the range of approximately 0.005 inches to 0.02 inches. The size, number, and/or positioning of the irrigation ports 30 can vary, however. In some embodiments, for example, the ablation electrode tip 28 further includes a number of fluid irrigation ports 30 located circumferentially about the tip 28 proximally of the laterally-facing ultrasonic imaging sensors 36b, 36c, 36d. During ablation therapy, the cooling fluid is used to control the temperature and reduce coagulum formation on the ablation electrode tip 28, thus preventing an impedance rise of the tissue in contact with the tip 28 and increasing the transfer of RF ablation energy delivered from the tip 28 into the tissue.

Figure 3:
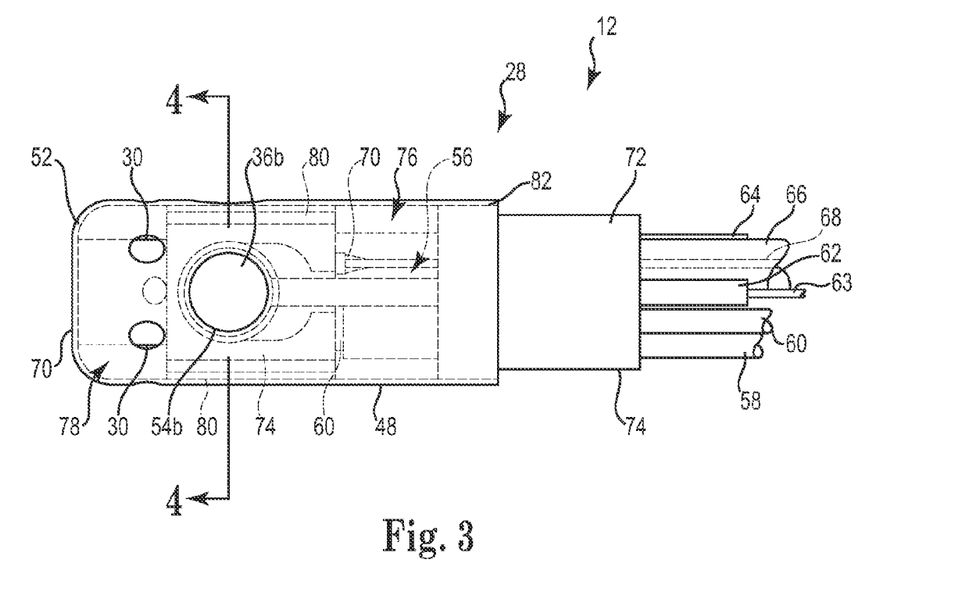
FIG. 3 is a cross-sectional view of the ablation electrode tip.

FIG. 3 is a cross-sectional view of the ablation electrode tip 28. As can be further seen in FIG. 3, the ablation electrode tip 28 includes an interior lumen 56 that houses the ultrasonic imaging sensors 36a, 36b, 36c, 36d, electrical conduits 58, 60, 62, 63 for transmitting power to and receiving signals back from the sensors 36a, 36b, 36c, 36d, and an electrical conduit 64 for supplying RF ablation energy to the RF electrode 48. In some embodiments, the electrical conduits 58, 60, 62, 63, 64 comprise insulated tubular members that contain wire leads used to electrically connect the RF generator 14 to the RF electrode 48 and the ultrasonic imaging module 18 to the ultrasonic imaging sensors 36a, 36b, 36c, 36d. A fluid conduit 66 extending through the probe 12 supplies cooling fluid from the fluid reservoir and pump 16 to the interior lumen 56 of the ablation electrode tip 28, which is then transmitted into the surrounding tissue through the irrigation ports 30. A thermocouple lead 68 extending through the probe 12 terminates distally at a thermocouple 70 located within the interior lumen 56 for sensing the temperature of the ablation electrode tip 28 during the ablation procedure.

A proximal tip insert 72 is used for coupling the ablation electrode tip 28 to the distal end 50 of the probe body 20. A distal tip insert 74 is configured to support the laterally-facing ultrasonic imaging sensors 36b, 36c, 36d within the ablation electrode tip 28, and divides the interior lumen 56 into a proximal fluid chamber 76 and a distal fluid chamber 78. A number of fluid channels 80 extending lengthwise along the length of the distal tip insert 74 fluidly connect the proximal fluid chamber 76 to the distal fluid chamber 78. During ablation, the presence of the distal tip insert 74 within the ablation electrode tip 28 creates a back pressure as the cooling fluid enters the proximal fluid chamber 76, causing the fluid to circulate before being forced through the channels 80 and into the distal fluid chamber 78.

Figure 4:
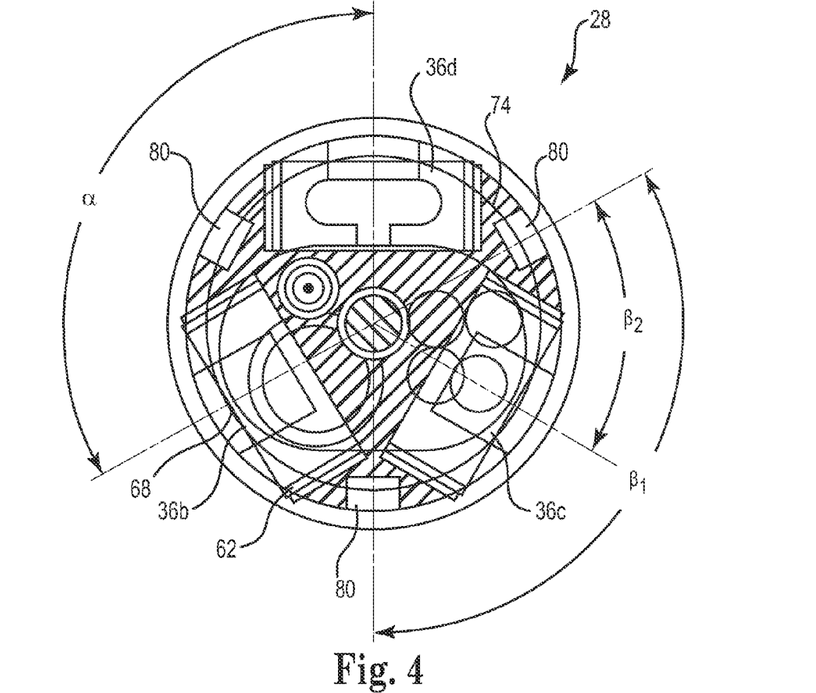
FIG. 4 is a cross-sectional view of the ablation electrode tip along line 4-4 in FIG. 2.

FIG. 4 is a cross-sectional view of the ablation electrode tip 28 along line 4-4 in FIG. 3. As can be further seen in conjunction with FIG. 4, and in some embodiments, the distal tip insert 74 includes three fluid channels 80 for supplying cooling fluid from the proximal fluid chamber 76 to the distal fluid chamber 78. As can be further seen in FIG. 4, and in some embodiments, the ablation electrode tip 28 includes three laterally-facing ultrasonic imaging sensors 36b, 36c, 36d equally spaced from each other at an angle α of 120° about the circumference of the distal tip insert 74. Although three laterally-facing ultrasonic sensors 36b, 36c, 36d are shown in the embodiment of FIG. 4, a greater or lesser number of ultrasonic imaging sensors may be employed. By way of example and not limitation, four ultrasonic imaging sensors may be disposed at equidistant angles α of 90° about the circumference of the distal tip insert 74. During imaging, the use of multiple laterally-facing ultrasonic imaging sensors 36b, 36c, 36d spaced about the circumference of the distal tip insert 74 ensures that the field of view of at least one of the sensors 36b, 36c, 36d is in close proximity to the target tissue irrespective of the tip orientation relative to the target tissue. Such configuration also permits the physician to easily visualize the target tissue without having to rotate the probe 12 once the probe 12 is in contact with the tissue.

To conserve space within the ablation electrode tip 28, the fluid channels 80 are each circumferentially offset from the ultrasonic imaging sensors 36b, 36c, 36d. In the embodiment shown in which three laterally-facing ultrasonic imaging sensors 36b, 36c, 36d are employed, each of the fluid channels 80 are disposed circumferentially at equidistant angles $\beta_1$ of 120° about the circumference of the distal tip insert 74, and are circumferentially offset from each adjacent ultrasonic imaging sensor by an angle R2 of approximately 60°. The angle $\beta_1$ between each of the fluid channels 80 and the angle $\beta_2$ between each fluid channel 80 and adjacent ultrasonic imaging sensor 36b, 36c, 36d can vary in other embodiments depending on the number of fluid channels and/or ultrasonic imaging sensors provided. In some embodiments, the fluid channels 80 each have an equal cross-sectional area and are equally positioned around the center of the distal tip insert 74. The number and configuration of the fluid channels can vary. In one embodiment, for example, the fluid channels are circumferentially aligned with the acoustic pathway of the ultrasonic imaging sensors in the manner described, for example, in co-related U.S. Pat. No. 8,945,015, entitled "Ablation Probe With Fluid-Based Acoustic Coupling For Ultrasonic Tissue Imaging," the contents of which are incorporated herein by reference in their entirety for all purposes.

Figure 5:
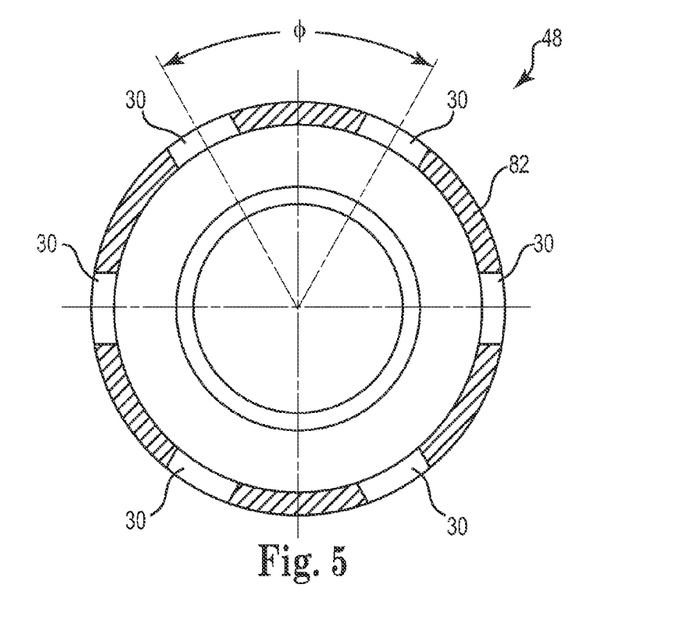
FIG. 5 is a cross-sectional view of the RF electrode along line 5-5 in FIG. 2.

FIG. 5 is a cross-sectional view of the RF electrode 48 along line 5-5 in FIG. 2. As can be further seen in FIG. 5, the RF electrode 48 comprises a tubular-shaped shell 82 including six irrigation ports 30 equally spaced from each other at an angle φ of 60° about the circumference of the shell 82. The number, size, and angle φ between each of the irrigation ports 30 can vary in other embodiments. To minimize interference of the irrigation fluid with the transmission of ultrasonic waves from the ultrasonic imaging sensors 36, and in some embodiments, the centers of the irrigation ports 30 are offset circumferentially from the centers of the side-facing acoustic openings 54b, 54c. In those embodiments in which the ablation electrode tip 28 includes three lateral-facing ultrasonic imaging sensors 36b, 36c, 36d and six irrigation ports 30, for example, the irrigation ports 30 can be circumferentially offset from each adjacent side acoustic opening 54b, 54c by an angle of approximately 30°. This circumferential offset may vary in other embodiments depending on the number and configuration of imaging sensors 36 as well as other factors. In some embodiments, the irrigation ports 30 are circular in shape, and have a diameter within a range of approximately 0.005 to 0.02 inches.

Figure 6:
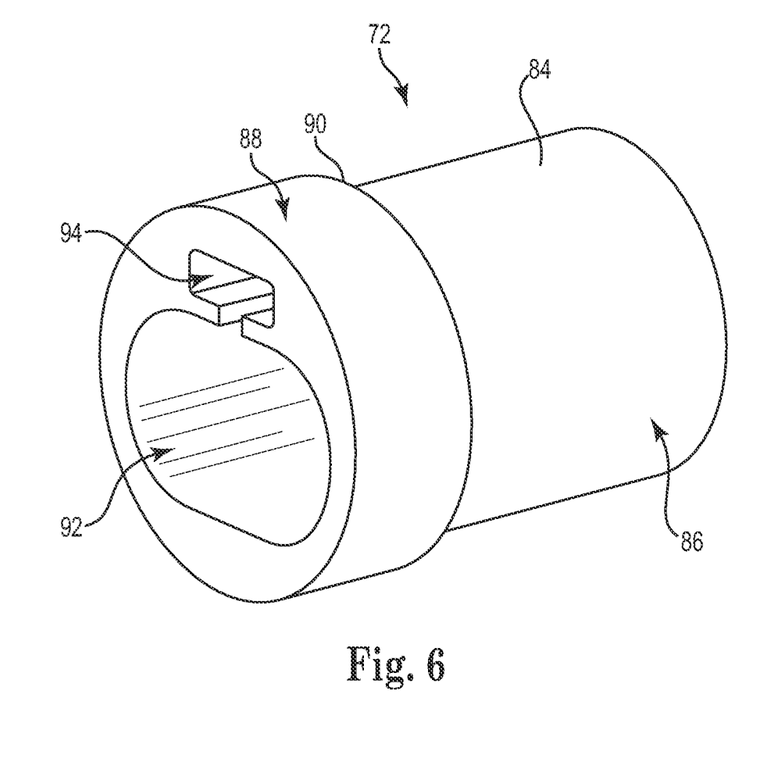
FIG. 6 is a perspective view of the proximal tip insert of FIG. 3.

FIG. 6 is a perspective view of the proximal tip insert 72 of FIG. 3. As can be further seen in FIG. 6, the proximal tip insert 72 comprises a hollow metal insert body 84 having a proximal section 86 and a distal section 88. The proximal section 86 is configured to attach to the distal end 50 of the probe body 20. The distal section 88, in turn, has an enlarged outer diameter relative to the proximal section 86, and is configured to attach to the RF electrode shell 82. In some embodiments, the proximal tip insert 72 is coupled to both the distal end 50 of the probe body 20 and to the RF electrode shell 82 via frictional fit, solder, welding, and/or an adhesive attachment. A shoulder 90 at the transition from the proximal section 86 to the distal section 88 serves as a flange to align the distal end 50 of the probe body 20 flush with the RF electrode shell 82.

A first lumen 92 disposed through the proximal tip insert 72 provides a conduit for the electrical and fluid conduits 58, 60, 62, 64, 66 that supply electrical signals and cooling fluid to the ablation electrode tip 28. A second lumen 94 disposed through the proximal tip insert 72 provides a conduit for the steering mechanism used for deflecting the probe 12.

Figure 7:
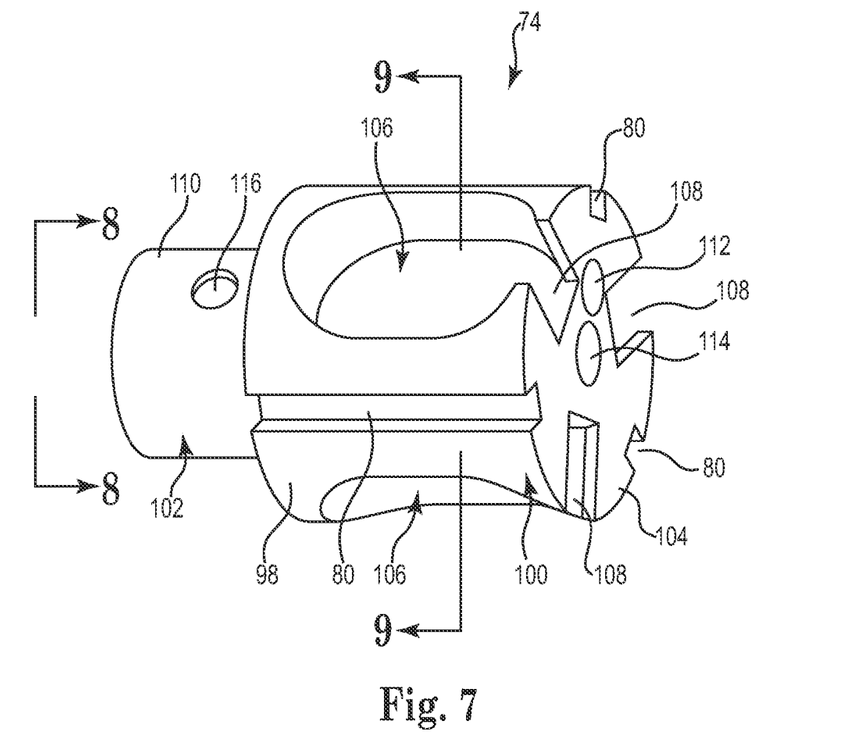
FIG. 7 is a perspective view of the distal tip insert of FIG. 3.

FIG. 7 is a perspective view of the distal tip insert 74 of FIG. 3. As shown in FIG. 7, the distal tip insert 74 comprises a cylindrically-shaped metal body 98 having a proximal section 100 and a distal section 102. In the embodiment of FIG. 7, the outer extent 104 of the proximal section 100 is sized to fit within the RF electrode shell 82 adjacent to the location of the side acoustic openings 54b, 54c, and includes three fluid channels 80. The outer extent 104 further includes a number of recesses 106 each configured to receive a corresponding one of the lateral-facing ultrasonic imaging sensors 36b, 36c, 36d therein. In some embodiments, the recesses 106 are sized and shaped to receive the ultrasonic imaging sensors 36b, 36c, 36d such that the sensors 36b, 36c, 36d lie substantially flush with the outer extent 104. An exposed opening 108 located at the proximal end of the distal tip insert 74 provides a channel to feed the electrical conduits for the ultrasonic imaging sensors 36b, 36c, 36d into the recesses 106.

The distal section 102 of the distal tip insert 74 is configured to support the distal-facing ultrasonic imaging sensor 36a within the ablation electrode tip 28. The outer extent 110 of the distal section 102 is reduced in diameter relative to the proximal section 100. This reduction in diameter creates an annular-shaped distal fluid chamber 78 (see FIG. 3) that receives cooling fluid via the fluid channels 80.

Figure 8:
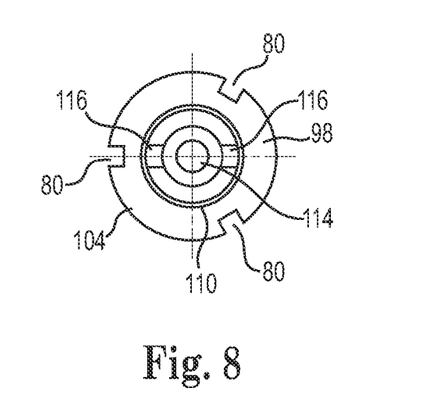
FIG. 8 is an end view of the distal tip insert of FIG. 7 along line 8-8 in FIG. 7.
Figure 9:
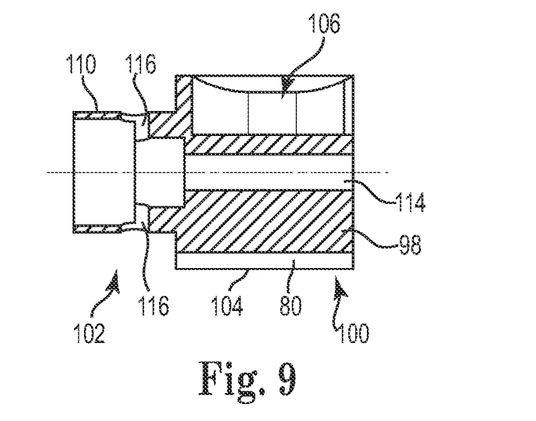
FIG. 9 is a cross-sectional view of the distal tip insert along line 9-9 in FIG. 7.

An aperture 112 within the proximal section 100 of the insert body 98 is configured to receive the distal end of a thermocouple used for sensing the temperature of the ablation electrode tip 28. As can be further seen in FIGS. 8-9, a second, central bore 114 extending through the proximal and distal sections 108, 110 of the insert body 104 is configure to receive the distal-facing ultrasonic imaging sensor 36a and a portion of the electrical conduit 63 that connects the sensor 36a to the ultrasonic imaging module 18. In some embodiments, a number of side apertures 116 disposed through the distal section 102 are used to permit alignment and mounting of the distal-facing ultrasonic imaging sensor 36a.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An ablation probe for treating and imaging body tissue, the ablation probe comprising:
    an ablation electrode tip including an ablation electrode configured for delivering ablation energy to body tissue;
    a plurality of acoustic openings disposed through the ablation electrode tip;
    a distal tip insert disposed within an interior lumen of the ablation electrode tip, the distal tip insert including a plurality of fluid channels; and
    a plurality of ultrasonic imaging sensors coupled to the distal tip insert, the ultrasonic imaging sensors configured to transmit ultrasonic waves through the acoustic openings, wherein the distal tip insert includes a plurality of recesses each configured for receiving one of the plurality of ultrasonic imaging sensors.

2. The probe of claim 1, wherein the ablation electrode tip comprises a tubular-shaped metal shell.

3. The probe of claim 1, wherein the interior lumen of the ablation electrode tip includes a proximal fluid chamber and a distal fluid chamber, and wherein the proximal and distal fluid chambers are separated by the distal tip insert and are fluidly coupled to each other via the fluid channels.

4. The probe of claim 1, wherein distal tip insert comprises a cylindrically-shaped insert body having a proximal section and a distal section.

5. The probe of claim 4, wherein the fluid channels extend lengthwise along the proximal section of the distal insert body.

6. The probe of claim 1, wherein the ultrasonic imaging sensors are disposed circumferentially about the distal tip insert.

7. The probe of claim 6, wherein the fluid channels are disposed circumferentially about the distal tip insert.

8. The probe of claim 7, wherein the fluid channels are circumferentially offset from the ultrasonic imaging sensors.

9. The probe of claim 1, further comprising an elongate probe body coupled to the ablation electrode tip.

10. The probe of claim 1, further comprising a proximal tip insert coupling a distal section of the elongate probe body to the ablation electrode tip.

11. The probe of claim 1, further comprising a plurality of irrigation ports disposed through the ablation electrode tip.

12. The probe of claim 11, wherein the irrigation ports are located about the ablation electrode tip distally and/or proximally of the acoustic openings.

13. The probe of claim 1, wherein the ultrasonic imaging sensors comprise a plurality of laterally-facing ultrasonic imaging sensors configured for transmitting ultrasonic waves from a side of the ablation electrode tip.

14. The probe of claim 13, wherein the literally-facing ultrasonic imaging sensors are each coupled to one of the plurality recesses within the distal tip insert.

15. The probe of claim 1, wherein the ultrasonic imaging sensors comprise at least one distally-facing ultrasonic imaging sensor configured for transmitting ultrasonic waves in a distal direction.

16. The probe of claim 15, wherein the distal-facing ultrasonic imaging sensor is coupled to an internal bore within the distal tip insert.

17. An ablation probe for treating and imaging body tissue, the ablation probe comprising:
    an elongate probe body having a proximal section and a distal section;
    an ablation electrode tip coupled to the distal section of the elongate probe body, the ablation electrode tip including an ablation electrode configured for delivering ablation energy to body tissue;
    a plurality of acoustic openings disposed through the ablation electrode tip;
    a distal tip insert disposed within an interior lumen of the ablation electrode tip, the distal tip insert separating the interior lumen into a proximal fluid chamber and a distal fluid chamber;
    a plurality of laterally-facing ultrasonic imaging sensors each coupled to a corresponding recess within the distal tip insert, the laterally-facing ultrasonic imaging sensors each configured to transmit ultrasonic waves from a side of the ablation electrode tip a plurality of fluid channels disposed about an outer extent of the distal tip insert and circumferentially offset from the ultrasonic imaging sensors; and a distally-facing ultrasonic imaging sensor coupled to the distal insert, the distally-facing ultrasonic imaging sensor configured for transmitting ultrasonic waves in a forward direction away from a distal end of the ablation electrode tip.

18. An ablation and ultrasound imaging system, comprising:

a probe configured for delivering ablation energy to body tissue, the probe comprising:

an ablation electrode tip;

a plurality of acoustic openings disposed through the ablation electrode tip;

a distal tip insert disposed within an interior lumen of the ablation electrode tip, the distal tip insert including a plurality of fluid channels; and a plurality of ultrasonic imaging sensors coupled to the distal tip insert, the ultrasonic imaging sensors configured to transmit ultrasonic waves through the acoustic openings, wherein the distal tip insert includes a plurality of recesses each configured for receiving one of the plurality of ultrasonic imaging sensors;

an ablation therapy module comprising an ablation source configured to generate and supply an electrical signal to the ablation electrode tip; and an ultrasound imaging module comprising an image processor configured to process ultrasonic imaging signals received from the ultrasonic imaging sensors to generate an ultrasonic image.

19. The system of claim 18, wherein the ultrasonic imaging module further comprises:

a signal generator configured to generate control signals for controlling each ultrasonic imaging sensor.

\* \* \* \* \*